United States Patent [19]

Takatsu et al.

[11] Patent Number: 5,315,024
[45] Date of Patent: May 24, 1994

[54] CYANO-SUBSTITUTED COMPOUND CONTAINING ETHER BOND

[75] Inventors: Haruyoshi Takatsu, Tokyo; Makoto Sasaki, Saitama; Kiyofumi Takeuchi, Tokyo, all of Japan

[73] Assignee: Dainippon Ink and Chemicals, Inc., Tokyo, Japan

[21] Appl. No.: 13,661

[22] Filed: Feb. 4, 1993

Related U.S. Application Data

[63] Continuation of Ser. No. 873,690, Apr. 24, 1992, abandoned, which is a continuation of Ser. No. 557,825, Jul. 26, 1990, abandoned.

[30] Foreign Application Priority Data

| Jul. 28, 1989 | [JP] | Japan | 1-196073 |
| Oct. 9, 1989 | [JP] | Japan | 1-262224 |
| Oct. 19, 1989 | [JP] | Japan | 1-272405 |
| Dec. 1, 1989 | [JP] | Japan | 1-312864 |
| Feb. 20, 1990 | [JP] | Japan | 2-39308 |

[51] Int. Cl.$^5$ ............................. C07C 255/54
[52] U.S. Cl. ........................ 558/423; 252/299.63
[58] Field of Search ......................... 558/423

[56] References Cited

U.S. PATENT DOCUMENTS

| 4,402,855 | 9/1983 | Zann et al. | 558/423 X |
| 4,468,340 | 8/1984 | Inoue et al. | 558/423 X |
| 4,536,321 | 8/1985 | Sugimori et al. | 558/423 X |
| 4,630,896 | 12/1986 | Petrzilka et al. | 558/423 X |
| 4,723,005 | 2/1988 | Huynh-Ba et al. | 558/423 X |
| 5,202,055 | 4/1993 | Uchida et al. | 558/423 X |

FOREIGN PATENT DOCUMENTS

| 119756 | 9/1984 | European Pat. Off. |
| 258868 | 3/1988 | European Pat. Off. |
| 360080 | 3/1990 | European Pat. Off. |
| 3237020 | 5/1983 | Fed. Rep. of Germany |
| 3906038 | 9/1989 | Fed. Rep. of Germany |
| 61-100548 | 5/1986 | Japan ......................... 558/423 |

*Primary Examiner*—Joseph Paul Brust
*Attorney, Agent, or Firm*—Armstrong, Westerman, Hattori, McLeland & Naughton

[57] ABSTRACT

A cyano-substituted compound containing an ether bond is described, which is represented by formula (I):

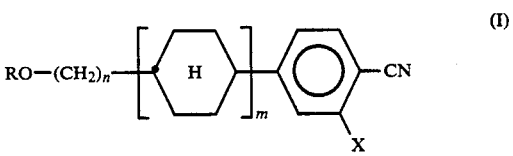

wherein R represents a straight-chain alkyl group having from 1 to 5 carbon atoms; X represents a hydrogen atom or a fluorine atom; n represents an integer of 2 to 8; m represents 1 or 2; and the cyclohexane ring is arranged at a trans-configuration.

10 Claims, No Drawings

CYANO-SUBSTITUTED COMPOUND CONTAINING ETHER BOND

This application is a continuation of Ser. No. 07/873,690, filed Apr. 24, 1992, now abandoned, which in turn is a continuation of Ser. No. 07/557,825filed Jul. 26, 1990, now abandoned.

FIELD OF THE INVENTION

The present invention relates to a cyano-substituted compound containing an ether bond useful as an electrooptical display material.

BACKGROUND OF THE INVENTION

Typical liquid crystal display cells include TN-LCD (twisted nematic liquid crystal display devices) which are utilized in the fields of clocks, watches, electronic calculators, electronic notebooks, pocket computers, word processors and personal computers. The information density on one display has been increased with an increase in information to be processed by OA apparatuses in recent years. Conventional TN-LCD can no longer meet requirements of high multiplex drive systems, particularly word processors and personal computers with respect to the quality level of visual field angle and contrast.

Under such circumstances, STN (super twisted nematic) -LCD have been developed by Scheffer et al (SID'85 Digest, p. 120 (1985)) and Kinukawa et al (SID'86 Digest, p. 122 (1986)) and are beginning to widely spread for use in display of high information processing in word processors and personal computers.

As one of a useful liquid crystal compound in a STN-LCD, there is a compound represented by

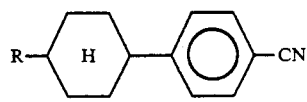

(wherein R represents a straight-chain alkyl group) (hereinafter referred to as PCH).

PCH is a useful P-type liquid crystal compound having positive dielectric anisotropy. But the dielectric anisotropy value ($\Delta\epsilon$) of PCH is not so large, as much as about +12 to 13. Thus there is disadvantageous in that when PCH is mixed with widely employed nematic liquid crystal materials, decrease in the threshold voltage of the liquid crystal material is small.

SUMMARY OF THE INVENTION

An object of the present invention is to provide a novel compound having a large dielectric anisotropy value ($\Delta\epsilon$) and, when mixed with a widely used nematic liquid crystal material, showing remarkable decrease in the threshold voltage of the liquid crystal.

In order to achieve the problem, the present invention provides a compound represented by formula (I):

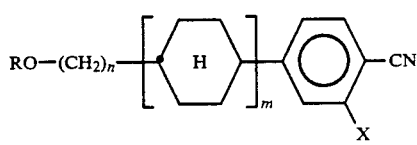

(I)

wherein R represents a straight-chain alkyl group having from 1 to 5 carbon atoms; X represents a hydrogen atom or a fluorine atom; n represents an integer of 2 to 8; m represents 1 or 2; and the cyclohexane ring is arranged at a trans-configuration.

DETAILED DESCRIPTION OF THE INVENTION

The compounds represented by formula (I) according to the present invention can be prepared, for example, by the following manufacturing procedure.

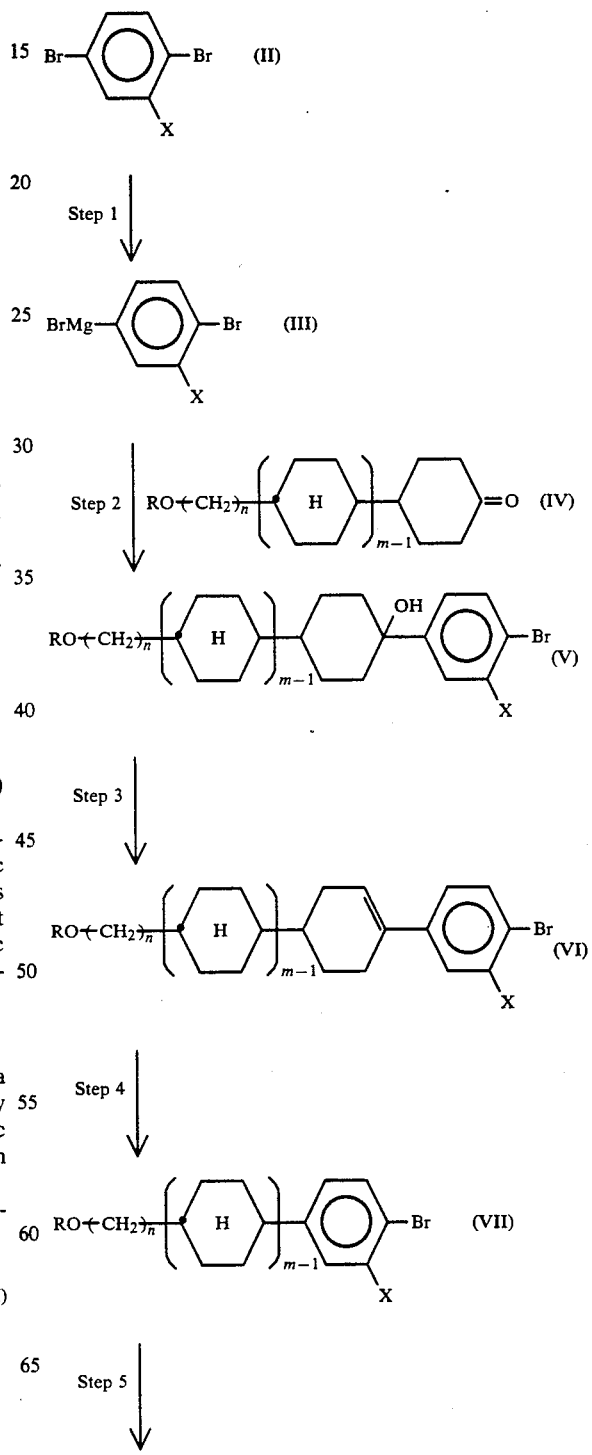

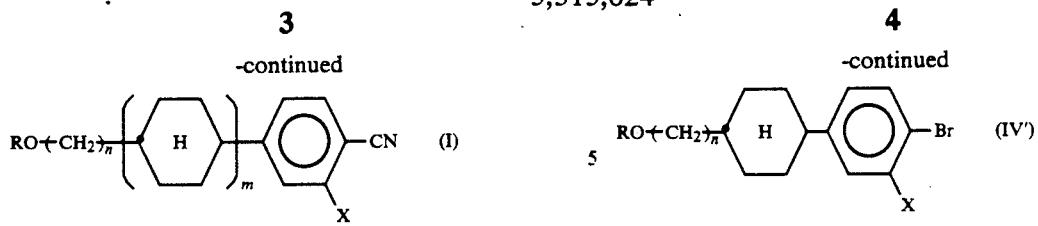

wherein R represents a straight-chain alkyl group having 1 to 5 carbon atoms; n represents an integer of 2 to 8; X represents a hydrogen atom or a fluorine atom; m represents 1 or 2; and the cyclohexane ring is arranged at a trans-configuration.

Step 1

A compound of formula (II) is reacted with a magnesium powder in tetrahydrofuran to obtain a grignard reagent of formula (III).

Step 2

The compound of formula (III) is reacted with a compound of formula (IV) in tetrahydrofuran to obtain a compound of formula (V).

Step 3

The compound of formula (V) is dehydrated in toluene in the presence of an acid catalyst, e.g., p-toluenesulfonic acid to obtain a compound of formula (VI).

Step 4

The compound of formula (VI) is catalytically reduced in an alcohol, e.g., ethanol in the presence of Raney nickel as a catalyst to obtain a compound of formula (VII).

Step 5

The compound of formula (VII) is reacted with a cuprous cyanide in a polar solvent, e.g., N,N-dimethylformamide to produce a compound of formula (I).

In formula (I), a compound where m is 1 can also be prepared by the following manufacturing procedure.

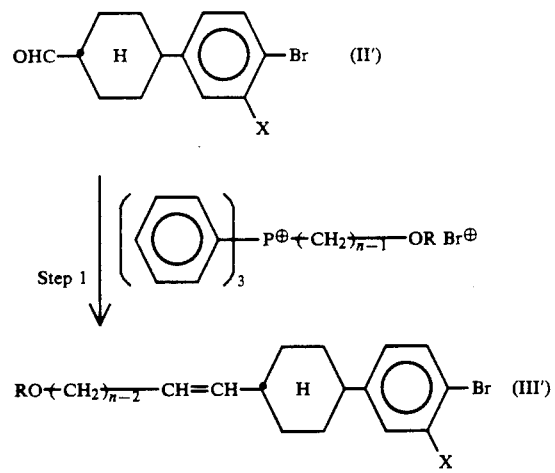

wherein R, n, and X are as defined above.

Step 1

A compound of formula (II') is subjected to witting reaction with alkoxymethyl-triphenyl phosphonium bromide in an ether solvent, e.g., t-butylmethyl ether to obtain a compound of formula (III').

Step 2

The compound of formula (III') is catalytically reduced in ethyl acetate in the presence of Raney nickel as a catalyst to obtain a compound of formula (IV').

Step 3

The compound of formula (IV') is reacted with a cuprous cyanide in a basic solvent, e.g., dimethylformamide to obtain a compound of formula (I).

Phase transition temperatures of typical compounds of formula (I) are listed in Table 1 below.

TABLE 1

| Compound No. | R | n | m | X | Phase Transition Temperature (°C.) |
|---|---|---|---|---|---|
| 1 | $CH_3$— | 2 | 1 | H— | 51 (C → I) |
| 2 | $C_2H_5$— | 2 | 1 | H— | 44 (C → I) |
| 3 | $CH_3$— | 3 | 1 | H— | 53 (C → N) |
|   |   |   |   |   | 56 (N ⇌ I) |
| 4 | $CH_3$— | 3 | 1 | F— | 41 (C → I) |
|   |   |   |   |   | 10 (I ⇌ N) |
| 5 | $CH_3$— | 3 | 2 | H— | 84 (C → N) |
|   |   |   |   |   | 237 (N ⇌ I) |
| 6 | $CH_3$— | 3 | 2 | F— | 82 (C → N) |
|   |   |   |   |   | 202 (N ⇌ I) |
| 7 | $CH_3$— | 5 | 2 | H— | 72 (C → N) |
|   |   |   |   |   | 232 (N ⇌ I) |
| 8 | $CH_3$— | 5 | 2 | F— | 69 (C → N) |
|   |   |   |   |   | 198 (N ⇌ I) |

Note: In Table 1, C represents a crystalline phase; N represents a nematic phase; and I represents an isotropic liquid phase.

The compounds of formula (I) according to the present invention are nematic liquid crystal compounds having a positive dielectric anisotropy. Thus it may be mixed with other nematic liquid crystal compounds(s) having a negative dielectric anisotropy and applied for a dynamic scattering mode display cell material. Alter- -continued

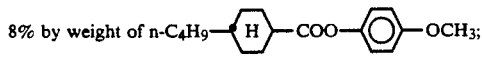
8% by weight of n-C₄H₉—⟨H⟩—COO—⟨O⟩—OCH₃;

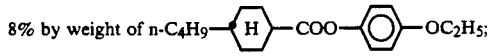
8% by weight of n-C₄H₉—⟨H⟩—COO—⟨O⟩—OC₂H₅;

8% by weight of n-C₅H₁₁—⟨H⟩—COO—⟨O⟩—OCH₃;

and

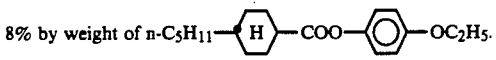
8% by weight of n-C₅H₁₁—⟨H⟩—COO—⟨O⟩—OC₂H₅.

The compound (c) is a known compound as described in U.S. Pat. No. 4,154,697 and DE 2,701,591 represented by:

TABLE 3

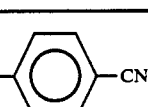

| | N-I point (°C.) | Viscosity (20° C.) | Threshold Voltage | Dielectric Anisotropy |
|---|---|---|---|---|
| (B) | 54.5 | 21.0 c.p. | 1.60 | 6.7 |
| (B) + No. 5 | 86.0 | 26.2 c.p. | 1.68 | 9.3 |
| (B) + No. 6 | 82.2 | 26.8 c.p. | 1.54 | 9.9 |
| (B) + No. 7 | 85.8 | 26.3 c.p. | 1.69 | 9.1 |
| (B) + No. 8 | 82.0 | 26.9 c.p. | 1.56 | 9.3 |
| (B) + (c) | 84.1 | 28.5 c.p. | 1.82 | 7.8 |

It is apparent from Table 3 that when the compound of formula (I) is added to the mixed liquid crystal (B), the compound of formula (I) increases the dielectric anisotropy and remarkably lowers the threshold voltage of the liquid crystal mixture, as compared with the compound (c) which is similar to the compound of the invention in structure. In addition, it can be understood from Table 3 that the compound of formula (I) remarkably increases the N-I point of the liquid crystal mixture and lowers the viscosity as compared with the compound (c) which is similar to the compound of the invention in structure.

The present invention is now illustrated in greater detail by way of the following Examples, but it should be understood that the present invention is not deemed to be limited thereto.

EXAMPLE 1

1.5 g (0.06 mol) of magnesium powder was added to 10 ml of absolute tetrahydrofuran (which will be called THF hereinafter) and the mixture was activated by a catalytic amount of dibromoethylene. Then to the mixture was dropwise added a solution of 14.2 g (0.06 mol) of the compound of formula:

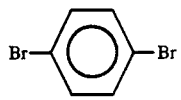
Br—⟨O⟩—Br diluted in 25 ml of absolute THF at 30° C. or lower. After the dropwise addition, stirring of the mixture was continued for 0.5 hour at the same temperature. Next, to the reaction solution was dropwise added a solution of 13.4 g (0.045 mol) of the compound of formula:

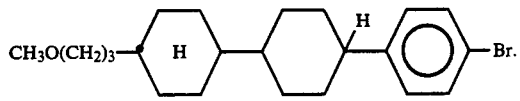
CH₃O(CH₂)₃—⟨H⟩—⟨H⟩=O dissolved in 40 ml of THF, and reacted for 5 hours at room temperature.

After the reaction, the reaction mixture was added to 50 ml of 9% hydrochloric acid, and extracted thrice with 120 ml of toluene. After the extract was washed with water and dried, the solvent was removed by distillation under reduced pressure to obtain 13.5 g (0.033 mol) of the following compound:

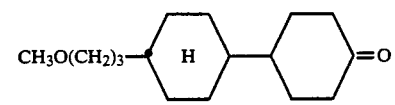
CH₃O(CH₂)₃—⟨H⟩—⟨H⟩—⟨O⟩—Br.

13.5 g of this compound was dissolved in 250 ml of toluene and 1 g of p-toluenesulfonic acid was added thereto, followed by heating under reflux for 4 hours while dehydrating by a dewatering apparatus. After the reaction, the toluene phase was washed with water and dried. Then the solvent was removed by distillation under reduced pressure to obtain a residue. The residue was separated and purified by chromatography on silica gel to obtain 8.5 g (0.022 mol) of the following compound:

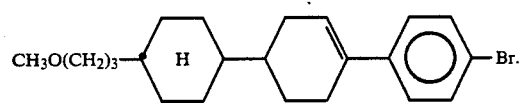
CH₃O(CH₂)₃—⟨H⟩—⟨ ⟩—⟨O⟩—Br.

8.5 g of this compound was dissolved in 250 ml of ethanol and 1 g of Raney nickel was added thereto, followed by catalytical reduction under hydrogen pressure of 5 kg/cm² for 13 hours at room temperature. After the reaction, the catalyst was separated by filtration and the ethanol was distilled off from the filtrate under reduced pressure to obtain a residue. The resulting residue was purified by recrystallization from 100 ml of n-hexane to obtain 6.7 g (0.017 mol) of the following compound:

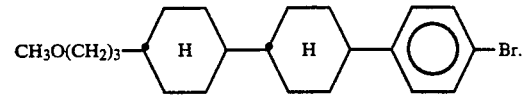
CH₃O(CH₂)₃—⟨H⟩—⟨H⟩—⟨O⟩—Br.

6.7 g of this compound was dissolved in 50 ml of dimethylformamide and 1.8 g (0.02 mol) of cuprous cyanide was added thereto, followed by heating under reflux for 10 hours. After the reaction, the reaction mixture was added to 100 ml of aqueous ammonia, stirred for 0.5 hour, and extracted thrice with 50 ml of ethyl acetate. The extract was washed with water and dried and the solvent was distilled off under reduced pressure to obtain a residue. The residue was purified by recrystallization from 60 ml of ethanol to obtain 3.8 g (0.011 mol) of the following compound:

natively, it may be mixed with other nematic liquid crystal compound(s) having a positive or negative dielectric anisotropy and applied for a field effect mode display cell material.

Typical examples of the compounds which can be preferably mixed with the compound of formula (I) include, for example, 4-substituted benzoic acid 4'-substituted phenyl esters, 4-substituted cyclohexanecarboxylic acid 4'-substituted phenyl esters, 4-substituted cyclohexanecarboxylic acid 4'-substituted biphenyl esters, 4-(4-substituted cyclohexanecarbonyloxy)benzoic acid 4'-substituted phenyl esters, 4-(4-substituted cyclohexyl)benzoic acid 4'-substituted phenyl esters, 4-(4-substituted cyclohexyl)benzoic acid 4'-substituted cyclohexyl esters, 4-substituted 4'-substituted biphenyls, 4-substituted phenyl-4'-substituted cyclohexanes, 4-substituted 4''-substituted terphenyls, 4-substituted biphenyl 4'-substituted cyclohexanes, 2-(4-substituted phenyl)-5-substituted pyrimidines.

Tables 2 shows the dielectric anisotropy and the threshold voltage of each liquid crystal mixture comprising 70% by weight of a mixed liquid crystal (A) which is widely employed in practice as a nematic liquid crystal material and 30% by weight of the compound of formula (I) Nos. 1 to 4 as shown in Table 1. Furthermore, the dielectric anisotropy of the mixed liquid crystal (A) and the dielectric anisotropy and the threshold voltage of each liquid crystal mixture comprising 70% by weight of the mixed liquid crystal (A) and 30% by weight of a compound (a) or (b) shown below which is similar to the compound of formula (I) in structure are shown in Table 2 for comparison.

The mixed liquid crystal (A) comprises:

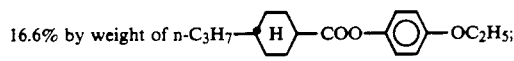

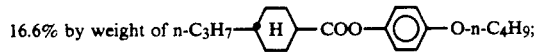

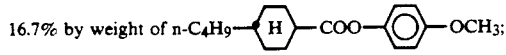

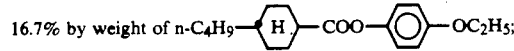

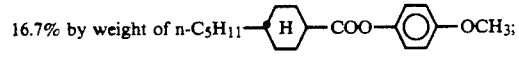

and

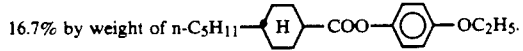

The compounds (a) and (b) are shown below.

TABLE 2

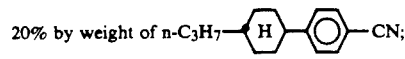

(a)

(b)

| Liquid Crystal | Dielectric Anisotropy | Threshold Voltage (V) |
|---|---|---|
| (A) | −1.3 | — |
| (A) + No. 1 | 4.0 | 1.43 |
| (A) + No. 2 | 3.8 | 1.46 |
| (A) + No. 3 | 5.1 | 1.70 |
| (A) + No. 4 | 7.1 | 1.36 |
| (A) + (a) | 3.8 | 2.00 |
| (A) + (b) | 1.5 | 2.18 |

It can be understood from Table 2 that when the compound of formula (I) is mixed with the mixed liquid crystal (A) having a negative dielectric anisotropy, the compound of formula (I) increases the dielectric anisotropy and lowers the threshold voltage of the liquid crystal mixture. As compared with the compound (a) which is similar to the compound of the invention in structure and widely employed in practice, it is clear that the compound of invention increases the dielectric anisotropy and remarkably lowers the threshold voltage of the liquid crystal mixture.

It could be understood that the present invention is not easily analogized by the skilled artisan because the decrease in the threshold voltage of the compound (b) which is a structural isomer of the compound of formula (I) is remarkably smaller than that of the compound Nos. 1 to 4 of the invention, still more, it is smaller than that of the compound (a).

Table 3 shows the N-I point, the viscosity, the threshold voltage, and the dielectric anisotropy (Δe) of each liquid crystal mixture comprising 80% by weight of a nematic mixed liquid crystal (B) which is widely employed in practice as a matrix liquid crystal and 20% by weight of the compound of formula (I), Nos. 5 to 8 as shown Table 1. For comparison, those of the mixed liquid crystal (B) and each liquid crystal mixture comprising 80% by weight of the mixed liquid crystal (A) and 20% by weight of the compound (c) as below are shown in Table 3.

The mixed liquid crystal (B) comprises:

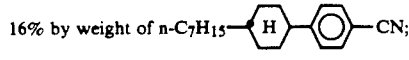

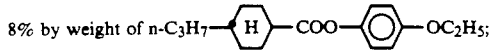

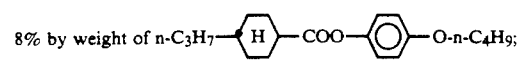

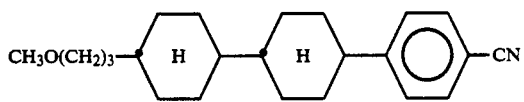

Transition temperature: 84° C. (C ⟶ N)

237° C. (N ⇌ I)

EXAMPLE 2

The procedure of Example 1 was repeated except that 15.3 g (0.06 mol) of a compound of the formula:

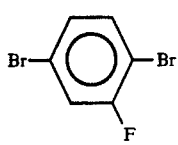

was used instead of the compound of formula:

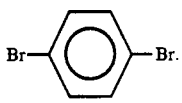

Thus the following compound was obtained.

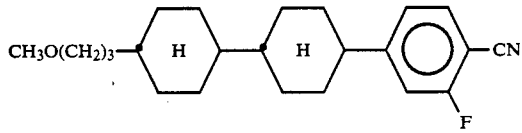

Transition temperature: 81° C. (C ⟶ N)

202° C. (N ⇌ I)

EXAMPLE 3

A compound of the following formula was obtained in the same manner as in Example 1.

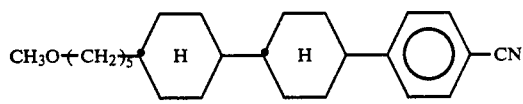

Transition temperature: 72° C. (C ⟶ N)

232° C. (N ⇌ I)

EXAMPLE 4

A compound of the following formula was obtained in the same manner as in Example 1.

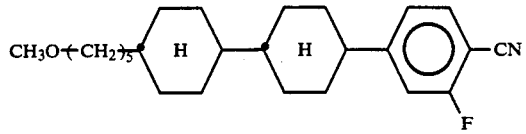

Transition temperature: 69° C. (C ⟶ N)

198° C. (N ⇌ I)

EXAMPLE 5

30.2 g (0.075 mol) of a compound of the formula:

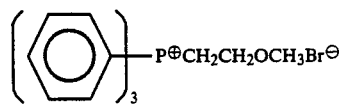

was added to 100 ml of t-butylmethyl ether, and the solution thus obtained was treated with 9 g (0.08 mol) of potassium t-butoxide under stirring at −10° C. After stirring for 10 minutes at the same temperature, the mixture was further stirred for 1 hour at room temperature. Next, after cooling the mixture to −5° C., a solution of 9.7 g (0.034 mol) of a compound of the formula:

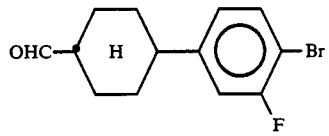

dissolved in 20 ml of THF was dropwise added to the resulting mixture for 5 minutes, then allowed to react for 1 hour at room temperature. After the reaction, to the reaction mixture was added 400 ml of water, and extracted thrice with 100 ml of ethyl acetate. After the organic layer was washed with water and dried, the solvent was distilled off under reduced pressure. The obtained residue was separated by chromatography on silica gel (eluent: n-hexane/toluene=1/1 by volume) to obtain 8.2 g (0.025 mol) of the following compound:

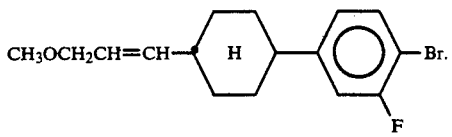

Next, 8.2 g of this compound was dissolved in 300 ml of 300 ml of ethyl acetate and 1 g of Raney nickel was added thereto as a catalyst, followed by catalytical reduction in an autoclave under hydrogen pressure of 5 kg cm$^2$.

After the reaction, the catalyst was separated by filtration and the solvent was distilled off from the filtrate under reduced temperature to obtain the 7.8 g (0.024 mol) of the following compound:

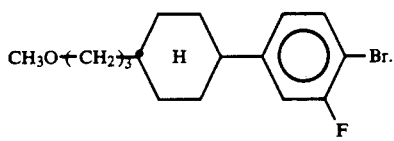

Next, 7.8 g (0.024 mol) of this compound was dissolved in 80 ml of dimethylformamide and 3.9 g (0.043 mol) of cuprous cyanide was added thereto, followed by heating under reflux for 4 hours. After the reaction, 100 ml of aqueous ammonia was added to the resulting mixture, and extracted with ethyl acetate. The extract was washed with water and dried and the solvent was distilled off under reduced pressure to obtain a residue. The residue was purified by recrystallization from ethanol to obtain 4.5 g (0.016 mol) of the following compound:

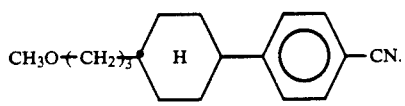

Transition temperature: 41° C. (C ⟶ I)

10° C. (I ⇌ N)

EXAMPLE 6

A compound of the following formula was obtained in the same manner as in Example 5.

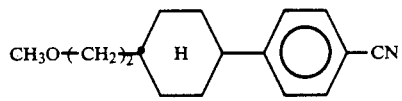

Melting point: 51° C.

EXAMPLE 7

A compound of the following formula was obtained in the same manner as in Example 5.

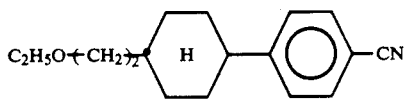

Melting point: 44° C.

EXAMPLE 8

A compound of the following formula was obtained in the same manner as in Example 5.

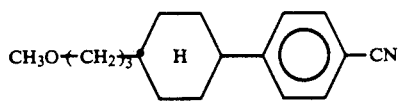

Transition temperature: 53° C. (C ⟶ N)

56° C. (N ⇌ I)

As described above, the compound of the present invention represented by formula (I), when mixed with a nematic liquid crystal material which is widely employed in practice increases the dielectric anisotropy and remarkably lowers the threshold voltage as compared with the compound which is similar to the compound of formula (I) in structure.

Therefore, the compounds of the present invention represented by formula (I) are very useful as materials for TN-LCD or STN-LCD.

While the invention has been described in detail and with reference to specific embodiments thereof, it will be apparent to one skilled in the art that various changes and modifications can be made therein without departing from the spirit and scope thereof.

What is claimed is:

1. A compound represented by formula (I):

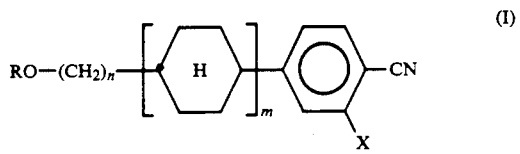

wherein R represents a straight-chain alkyl group having from 1 to 5 carbon atoms; X represents a hydrogen atom or a fluorine atom; n represents an integer of 2 to 8; m represents 1 or 2; and the cyclohexane ring is arranged at a trans-configuration.

2. A compound as claimed in claim 1, wherein m is 1.
3. A compound as claimed in claim 2, wherein n is 2 or 3.
4. A compound as claimed in claim 3, wherein R is a methyl group.
5. A compound as claimed in claim 1, wherein m is 2.
6. A compound as claimed in claim 5, wherein n is 3.
7. A compound as claimed in claim 6, wherein R is a methyl group.
8. A compound as claimed in claim 5, wherein n is 5.
9. A compound as claimed in claim 8, wherein R is a methyl group.
10. A compound as claimed in claim 1, wherein X is fluorine.

* * * * *